United States Patent [19]

Choksi

[11] 4,152,783

[45] May 8, 1979

[54] LUBRICANT FOR SURGEON'S GLOVES AND METHOD OF APPLYING SAME

[75] Inventor: Pradip V. Choksi, Northridge, Calif.

[73] Assignee: American Hospital Supply Corporation, Evanston, Ill.

[21] Appl. No.: 843,401

[22] Filed: Oct. 19, 1977

[51] Int. Cl.² .................. A41D 19/00; A61B 19/00
[52] U.S. Cl. ................................. 2/168; 128/1 R; 424/69
[58] Field of Search ............ 128/1 R; 424/69; 2/168; 239/8

[56] References Cited

U.S. PATENT DOCUMENTS

| | | | |
|---|---|---|---|
| 2,507,244 | 5/1950 | Correll | 2/168 X |
| 2,621,333 | 12/1952 | Thomas et al. | 2/168 |
| 3,799,438 | 3/1974 | Shockley | 239/8 |
| 3,810,458 | 5/1974 | Semp | 128/1 R |
| 3,846,382 | 11/1974 | Ramsey | 128/1 R X |

*Primary Examiner*—Robert E. Bagwill
*Attorney, Agent, or Firm*—Larry N. Barger

[57] ABSTRACT

A surgeon's glove having a surface adapted to fit against the surgeon's hand. A coating of a water-soluble innocuous powder, such as sodium bicarbonate, having a particle size in the range of 2 to 30 microns. The powder is applied to a rubber surgeon's glove during a heat cure cycle while the glove is at a temperature in the range of 170° F. to 210° F., and the glove is sufficiently tacky to stick to a substantial portion of the powder, but not sufficiently wet to dissolve the powder.

5 Claims, No Drawings

LUBRICANT FOR SURGEON'S GLOVES AND METHOD OF APPLYING SAME

BACKGROUND

It is well-known to apply lubricating powders to surgeon's gloves to make an inner surface more slippery to aid in donning. It is almost impossible to don a commercially available rubber surgeon's glove without a lubricating powder.

A glove lubricating powder has to meet several criteria, i.e. capable of sterilization, stand-up under storage, be comfortable to the surgeon, provide a mechanical sliding surface, etc. Because of the problems reported in the literature with the insoluble talc material used in the past in gloves, various alternatives have been proposed to the water-insoluble lubricating powders. Talc has been reported as causing granuloma when small particles of the powder remain in the surgical wound.

It has also been proposed to use powdered polyglycolic acid (U.S. Pat. No. 3,810,458) which would become completely absorbed in the living tissue within 90 days in an effort to overcome granuloma problems. Various other powders of the absorbable type have been used in gloves, including cornstarch.

In an article entitled "The Talcum Powder Problem In Surgery And Its Solution," by Seelig et al in J.A.M.A., Dec. 11, 1943, numerous powders were listed as possible alternatives for talc, with the result that potassium bitartrate was proposed because it had sufficient insolubility to maintain its powdering effect after exposure to moisture. Sodium bicarbonate was dismissed after testing because it was not sufficiently insoluble. It is possible that is also failed because it gave such a grainy feel to the surgeon, even though no article size was given in the test. Currently, the smallest commercially available sodium bicarbonate powder has a particle size of 100 to 200 micron.

SUMMARY OF THE INVENTION

The present invention involves the unexpected discovery that a water-soluble innocuous powder can be used in particle sizes less than 30 micron without prematurely dissolving, and yet provide a good mechanical slippery surface. The water-soluble powder is secured to the surgeon's glove by applying it during a heat cure cycle while the glove is tacky enough to adhere to the powder, but not wet enough to dissolve the powder.

DETAILED DESCRIPTION

Because water-soluble powders, such as sodium bicarbonate, sodium chloride, and potassium chloride, dissolve quickly in water, it would be expected that very small particle sizes would dissolve quickly and would be inoperative as a glove lubricant.

Crystalline sodium bicarbonate powder having particle size in the range of 100 to 200 micron (the smallest commercially available) was crushed in a ball mill to reduce the particle size to approximately 10 micron. Although 5 to 15 micron is preferred, the particle size could be from 2 micron to 30 micron size. The small particles of sodium bicarbonate were wiped onto a rubber glove as it was exiting a cure oven at temperatures of approximately 190° F. Temperatures of 170° F. to 210° F. could be used. During the complete curing cycle, the glove may reach a peak temperature of 300° F., but the oven exit temperature was much lower and in the above mentioned range. As the glove exited the cure oven, it was sufficiently tacky to adhere to the sodium bicarbonate particles, but was not sufficiently wet to dissolve them. The particles were bonded to the glove by partially imbedding in the glove's surface. Subsequent subjection of the glove to ethylene oxide sterilization showed that the powder was still intact.

During the donning procedure, the tiny sodium bicarbonate particles stayed intact sufficiently long for the particles to provide their lubricating effect. Once donned, however, the very small amount of perspiration from the surgeon's fingers inside the gloves begins very quickly to wet and dissolve the sodium bicarbonate powder. This can be seen by a color change that starts to occur very quickly in the fingertips.

Additional tests were run using sodium chloride and potassium chloride with essentially the same results. While the above examples of water-soluble powders have been given, other water-soluble powders could be used in this size range.

The above invention provides for the first time a water-soluble glove lubricating powder with a particle size less than 30 micron. All previous glove lubricants, such as talc, cornstarch, etc., in this size range have not been readily soluble in water. The small water-soluble particles do have the unexpected capability of withstanding the rigors of manufacturing application, dry sterilization, storage, and remain intact during the period of donning, which must last several seconds.

The very small water-soluble particles of this invention are innocuous to human tissue, and it is noted that many of the examples, i.e. potassium chloride, sodium chloride, as well as sodium bicarbonate, are contained in blood.

In the above description, specific examples have been used to describe the invention. However, it is understood that persons skilled in the art can make modifications to these examples without departing from the spirit and scope of the invention.

I claim:

1. A surgeon's glove having a surface adapted to fit against the surgeon's hand, which surface is coated with a water-soluble tissue innocuous powder that has a particle size in the range of 2 to 30 micron.

2. A surgeon's glove having on a surface adapted to fit against the surgeon's hand a coating of sodium bicarbonate powder with a particle size of 5 to 15 micron; and a sufficient amount of this powder is bonded to the glove surface to maintain an easy lubricated donning characteristic of the glove and prevent shifting of such powder.

3. A surgeon's glove as set forth in claim 2, wherein the bonding is by a partial imbedding of the powder in the glove surface.

4. A surgeon's glove having a surface adapted to fit against a surgeon's hand, which surface is coated with a water-soluble tissue innocuous powder having a particle size less than 30 micron.

5. A surgeon's glove as set forth in claim 4, wherein the water-soluble powder is selected from the group consisting of sodium bicarbonate, sodium chloride, and potassium chloride.